(12) United States Patent
Tanno et al.

(10) Patent No.: US 6,171,616 B1
(45) Date of Patent: Jan. 9, 2001

(54) SOLID PREPARATION AND A METHOD OF MANUFACTURING IT

(75) Inventors: Fumie Tanno; Hiroyasu Kokubo, both of Kubiki-mura (JP)

(73) Assignee: Shin-Etsu Chemical Co., Ltd., Tokyo (JP)

(*) Notice: Under 35 U.S.C. 154(b), the term of this patent shall be extended for 0 days.

(21) Appl. No.: 09/287,640

(22) Filed: Apr. 7, 1999

(30) Foreign Application Priority Data

Apr. 13, 1998 (JP) ................................. 10-117780

(51) Int. Cl.[7] ........................... A61K 9/16; A61K 9/20
(52) U.S. Cl. ..................... 424/465; 424/464; 424/499; 514/961
(58) Field of Search ........................... 424/499, 464, 424/465, 468, 469, 470, 489; 514/961

(56) References Cited

U.S. PATENT DOCUMENTS

T913,006 * 8/1973 Lynch ................................. 260/17 R
4,756,911 7/1988 Drost et al. .
5,476,668 12/1995 Kobayashi et al. .
5,681,382 10/1997 Kokubo .

FOREIGN PATENT DOCUMENTS 1360126 7/1974 (GB) .

* cited by examiner

Primary Examiner—Robert H. Harrison
(74) Attorney, Agent, or Firm—Townsend & Banta

(57) ABSTRACT

A solid preparation characteristically containing for a binder methyl cellulose whose MeO content is 27.5–31.5 wt % and whose 2 wt % aqueous solution has a viscosity of 2–12 cP at 20° C.

The present invention can provide a solid preparation which has an adequate hardness and at the same time disintegrates quickly for easy absorption.

8 Claims, No Drawings

SOLID PREPARATION AND A METHOD OF MANUFACTURING IT

RELATED APPLICATION

This application claims the priority of Japanese Patent application No. 10-117780 filed on Apr. 13, 1998, which is incorporated herein by reference.

BACKGROUND OF THE INVENTION

1. Field of the Invention

This invention relates in general to a solid preparation for medicinal tablets, granules, and such, as well as a method of manufacturing it, and more particularly to a solid preparation which contains for a binder or a disintegrant methyl cellulose whose MeO content and aqueous solution viscosity are in specified ranges, as well as a method of manufacturing it.

2. The Prior Art

Solid preparations such as medicinal granules and tablets have advantages in that they are convenient for administering and easy to take.

However, a solid preparation may be worn away during transportation unless it has an adequate hardness; on the other hand if it is too hard then it may not disintegrate and be absorbed after it is inside the body.

In order to improve the hardness and the disintegration properties required of such a solid preparation, it is desirable to improve additives such as binders and disintegrants to be blended in the solid preparation.

Conventionally known substances for the binder of a solid preparation include methyl cellulose, hydroxypropylmethyl cellulose, hydroxypropyl cellulose, and polyvinylpyrolidone (hereafter abbreviated as MC, HPMC, HPC, and PVP).

Of these binders, MC is used as an additive for medicinal drugs which is a stable binder over a wide range of pH.

For example, Japanese unexamined patent publication Tokkai Hei 4-164025 reports to the effect that MC whose 2 wt % aqueous solution is 80 cP or higher at 20° C. can be used for the matrix base agent for controlled release tablets.

Solid preparations are mainly manufactured by the wet granulation method. Depending on the drug, an adequate hardness cannot be obtained by a normal amount of binder. If the amount to be added is increased to solve this problem, then although an increase in the hardness is achieved there is a problem in that the disintegration time in the body becomes longer.

Therefore, the development of a solid preparation containing a binder which quickly disintegrates even if the amount to be added is increased has been desired.

As for the MC, the commercially available low viscosity product has a viscosity of 15 cP, which is high. If this is used to prepare an aqueous solution of the binder such that an adequate hardness can be achieved, then the viscosity will be higher than 600 cP. In general, the viscosity of an aqueous solution used in the wet granulation method is 600 cP or less. Therefore, there is a problem in that this low viscosity product pushes the viscosity of the binder aqueous solution too high and hence denies the option of increasing the amount to be added to the solid preparation.

Furthermore, in the case where the MC is used in a powder form to granulate a solid preparation using water, there is also a problem in that dissolution of the MC powder takes time because of its high viscosity.

Based on the aforementioned problems, the inventors conducted earnest research to obtain a solid preparation which has an adequate hardness and at the same time disintegrates quickly, and discovered that the aforementioned problems can be solved by adding, for a binder or disintegrant, a MC whose MeO content and aqueous solution viscosity are in specific ranges to the solid preparation, thus completing the present invention.

The object of the present invention is to provide a solid preparation which has an adequate hardness and at the same time disintegrates quickly for easy absorption, as well as a method of manufacturing it.

BRIEF SUMMARY OF THE INVENTION

That is, the present invention provides a solid preparation characteristically containing for a binder methyl cellulose whose MeO content is 27.5–31.5 wt % and whose 2 wt % aqueous solution has a viscosity of 2–12 cP at 20° C.

Also, the present invention provides said solid preparation wherein said methyl cellulose content is 0.5–10 wt % of the solid preparation.

Furthermore, the present invention provides a method of manufacturing a solid preparation for granulating active ingredients which is a method of manufacturing said solid preparation wherein methyl cellulose which has a MeO content of 27.5–31.5 wt % and whose 2 wt % aqueous solution has a viscosity of 2–12 cP at 20° C. is added as a binder for granulation.

DETAILED DESCRIPTION OF THE INVENTION

The configuration of the present invention is described below.

The characteristics of the present invention are a solid preparation prepared by adding, for a binder, methyl cellulose whose MeO content is 27.5–31.5 wt % and whose 2 wt % aqueous solution has a viscosity of 2–12 cP, preferably 2–5 cP, at 20° C. during the granulation process of the solid preparation, as well as the fact that the binder contained in the solid preparation acts as a disintegrant at the same time.

Conventionally, there have been examples of MC with a MeO content of 27.5–31.5 wt % used as the film agent on the surface of a solid preparation (Tokkai Sho 60-84215 and Tokkai Sho 60-13719) wherein the viscosity of its 2 wt % aqueous solution was 3–15 cP. However, the present invention is the first case where MC whose MeO content is 27.5–31.5 wt % and whose 2 wt % aqueous solution has a viscosity of 2–12 cP at 20° C. is added during the granulation process and used as a binder which is contained inside.

The MC used in the present invention has an advantage in that, in the wet granulation method where it is used in the form of an aqueous solution, it can evenly spread all over the granulation powder and it can be used in a high concentration.

Also in the wet granulation method where the binder MC is added in the form of powder and granulation is carried out using water, a solid preparation with superior binding properties and also satisfactory disintegrating properties can be obtained even if a large amount is added, due to its high solubility in water.

In the present invention, it is not suitable to use MC with a 2 wt % aqueous solution viscosity higher than 12 cP because then the controlled release effect becomes too strong.

A commercial product manufactured and distributed by the applicant of the present invention can be used for the MC which has the aforementioned specific MeO content and viscosity range. The viscosity grade of the MC to be added can be selected from within the aforementioned viscosity range according to the solubility of the active ingredient in water.

The blend ratio of the aforementioned MC in the solid preparation is preferably 0.5–10 wt %, more preferably 1–5 wt %, of the total solid preparation. Acceptable blend ratios include those which allow granulation when manufacturing the solid preparation and give adequate disintegration properties to the solid preparation. More than 10 wt % MC is not preferable because then release of the active ingredient in the solid preparation slows down and the viscosity of the granulation material during the granulation process significantly increases, making it impossible to achieve even granulation.

In addition to the aforementioned MC and the active ingredient, the solid preparation of the present invention can contain other additives which are normally added during the manufacturing process of a solid preparation. Examples of these excipients such as lactose, starch and its derivatives, powder cellulose, crystalline cellulose, and calcium hydrogen phosphate, as well as lubricants such as magnesium stearate, calcium stearate, and talc. Furthermore, other binders, disintegrants, surfactants, coloring agents, sweetening agents, perfumes, etc. can be added as necessary.

The solid preparation of the present invention can be manufactured using conventional manufacturing methods such as the stirring-granulation method and the fluidized bed granulation method. The granulated solid preparation can be mixed with a lubricant and tablets can be formed by using a tablet machine in a conventional manner.

In the method of manufacturing the solid preparation of the present invention, the method of adding the MC for granulation is not limited, and examples include a method in which the MC powder is added to the mixed powder of the active ingredient, filler, and such, followed by granulation, as well as a method in which an aqueous solution prepared by dissolving the MC beforehand is added to the mixed powder of the active ingredient, filler, and such for granulation.

The solid preparation of the present invention thus obtained has superior binding properties and disintegrating properties, as shown in Examples below. Therefore, a superior solid preparation can be provided which, not like the solid preparations using MC with conventional MeO content and aqueous solution viscosity ranges, has high binding properties and quick disintegration properties.

The present invention can provide a solid preparation which has an adequate hardness and at the same time disintegrates quickly for easy absorption. The manufacturing method of the present invention improves the solubility of the binder to allow even granulation so that superior binding properties and adequate disintegration properties can be given to the preparation.

EXAMPLES

The present invention is described by referring to Examples and Comparative examples. The present invention is not limited to the following examples.

Example 1

A composition with the following recipe was mixed for 30 seconds using a vertical granulater (FM-VG-05 for Powrex corporation) with a blade speed of 700 rpm and chopper speed 3,000 rpm, 80.0 g of water was added in 10 seconds, and additional mixing was conducted for 10 minutes for granulation. The obtained granulate was dried overnight at 40° C. and sifted through a 20-mesh sieve to obtain granules for making tablets which is the solid preparation of the present invention.

| | |
|---|---|
| Lactose | 268.8 g |
| (Trade name "Pharmatose 200M" from DMV International) | |
| Corn starch | 115.2 g |
| (Trade name "Nisshoku Corn Starch W" from Nihon Shokuhin Kako Co., Ltd.) | |
| Microcrystalline cellulose | 10.0 g |
| (Trade name Avicel PH-101 from Asahi Chemical Industry Co., Ltd.) | |
| MC | 12.0 g |
| (Trade name "Metolose SM-4" from Shin-Etsu Chemical Co., Ltd., with a MeO content of 28.2 wt %, a 2 wt % aqueous solution viscosity of 4.1 cP at 20° C.) | |
| Water | 80.0 g |

Mg stearate in the amount of 0.5 wt %, for a lubricant, was added to the obtained granules for making tablets, and mixed in a plastic bag. This mixture was used to pressure-mold tablets of the solid preparation of the present invention under the following conditions. The physical properties of the tablets were compared by conducting the hardness test and JP disintegration test. The test results are shown in Table 1.

Conditions for Making Tablets
  Punch: 8 mm diameter, 6 mm R
  Tablet weight: 200 mg/Tablet
  Pressure for making tablets:
    Main-compression force: 1.5 t/p,
    Pre-compression force: 0.5 t/p

Example 2

Tablets were prepared and tested in the same manner as in Example 1 except for the fact that the amount of the binder MC to be added was changed to 20.0 g. The test results are shown in Table 1.

Comparative Example 1

Tablets were prepared and tested in the same manner as in Example 1 except for the fact that the binder MC in Example 1 was replaced by MC with a higher viscosity (Trade name "Metolose SM-15" from Shin-Etsu Chemical Co., Ltd. with a 2 wt % aqueous solution viscosity of 15.8 cP at 20° C). The test results are shown in Table 1.

Comparative Example 2

Tablets were prepared and tested in the same manner as in Example 1 except for the fact that the binder MC in Example 1 was replaced by 20.0 g of the MC used in Comparative example 1. The test results are shown in Table 1.

Comparative Example 3

Tablets were prepared and tested in the same manner as in Example 1 except for the fact that the binder MC in Example 1 was replaced by 20.0 g of HPMC (Trade name "TC-5E" ("Pharmacoat 603") from Shin-Etsu Chemical Co., Ltd. with a 2 wt % aqueous solution viscosity of 3.22 cP at 20° C.). The test results are shown in Table 1.

Comparative Example 4

Tablets were prepared and tested in the same manner as in Example 1 except for the fact that the binder MC in Example 1 was replaced by 20.0 g of HPC (Trade name "HPC EF-P" from Shin-Etsu Chemical Co., Ltd. with a 2 wt % aqueous solution viscosity of 5.56 cP at 20° C). The test results are shown in Table 1.

TABLE 1

|  | Example | | Comparative example | | | |
| --- | --- | --- | --- | --- | --- | --- |
|  | 1 | 2 | 1 | 2 | 3 | 4 |
| Tablet hardness (kgf) | 3.95 | 8.52 | 8.97 | 6.23 | 7.50 | 6.50 |
| Disintegration time (min) | 1.7 | 1.8 | 4.5 | 10.3 | 15.4 | 7.0 |

Table 1 shows that the tablets of Examples 1 and 2 which used MC whose MeO content is 27.5–31.5 wt % and whose 2 wt % aqueous solution has a viscosity of 2–12 cP at 20° C. exhibit a high hardness and a short disintegration time, indicating superior effects in terms of the binding properties and the disintegration properties.

Example 3

A composition with the following recipe was used in stirring granulation with the same granulation method as that of Example 1 to obtain granules for making tablets which are the solid preparation of the present invention.

| | |
| --- | --- |
| Lactose (Trade name "Pharmatose 2001M" from DMV International) | 90.0 parts |
| Low substituted HPC (Trade name "L-HPC LH-11" from Shin-Etsu Chemical Co., Ltd.) | 5.0 parts |
| MC (Trade name "Metolose SM-4" from Shin-Etsu Chemical Co., Ltd., with a MeO content of 28.2 wt %, a 2 wt % aqueous solution viscosity of 4.1 cP at 20° C.) | 5.0 parts |
| Water | 20.0 parts |

The obtained granules were used to make tablets under the same conditions as in Example 1, and the hardness test using an Erweka hardness tester and JP disintegration test were carried out. Each type of tablets were then stored for two months under heated and moistened conditions at a temperature of 40° C. and a relative humidity of 75%. At the one and two month points the hardness test and the disintegration test were conducted to test the stability of the tablets. The results are shown in Table 2.

Comparative Example 5

Tablets were prepared and tested in the same manner as in Example 3 except for the fact that the binder MC in Example 3 was replaced by MC with a higher viscosity (SM-15) used in Comparative example 1. The test results are shown in Table 2.

Comparative Example 6

Tablets were prepared and tested in the same manner as in Example 3 except for the fact that the binder MC in Example 3 was replaced by HPC used in Comparative example 4. The test results are shown in Table 2.

Comparative Example 7

Tablets were prepared and tested in the same manner as in Example 3 except for the fact that the binder MC in Example 3 was replaced by HPMC used in Comparative example 3. The test results are shown in Table 2.

TABLE 2

|  | Hardness (kgf) | | | Disintegration time (min) | | |
| --- | --- | --- | --- | --- | --- | --- |
|  | Initial | One month | Two month | Initial | One month | Two month |
| Example 3 | 6.4 | 6.8 | 6.6 | 1.2 | 1.6 | 1.2 |
| Comparative example 5 | 5.6 | 5.6 | 4.8 | 7.5 | 7.2 | 7.2 |
| Comparative example 6 | 6.9 | 10.0 | 9.6 | 7.5 | 21.2 | 22.3 |
| Comparative example 7 | 6.7 | 7.5 | 8.0 | 11.7 | 15.7 | 15.8 |

Table 2 indicates that the tablets of Examples 3 which used MC whose MeO content is 27.5–31.5 wt % and whose 2 wt % aqueous solution has a viscosity of 2–12 cP at 20° C. exhibit superior stability in terms of the binding properties and the disintegration properties.

Example 4

After preparing the binder solution (viscosity: 500 cP) by changing the amount of the MC (SM-4) to be added in Example 1 to 9.0 g in 80 g water, the granulation was carried out in the same manner as in Example 1. Using the obtained granulate, tablets were made using the same recipe as in Example 1 and the tablet hardness was tested.

Tablet Hardness: 12.6 kgf

Comparative Example 8

After preparing the binder solution (viscosity: 500 cP) by changing the amount of the MC (SM-15) to be added in Comparative example 1 to 5.0 g in 80 g water, the granulation was carried out in the same manner as in Example 1. Using the obtained granulate, tablets were made using the same recipe as in Example 1 and the tablet hardness was tested.

Tablet Hardness: 1.5 kgf

When solutions with the same viscosity are prepared, the case where SM-15 is used has a lesser amount of the binder and hence the hardness of the tablets is insufficient, whereas such a problem is solved when SM-4 is used.

What is claimed is:

1. A solid preparation comprising a granulated mixture of an active ingredient and a methyl cellulose binder with an MeO content of 27.5–31.5, wt %, wherein a 2 wt % aqueous solution of said methyl cellulose has a viscosity of 2–12 cP at 20° C.

2. The solid preparation of claim 1 wherein said methyl cellulose is present in a blend ratio of 0.5–10 wt % of the solid preparation.

3. A method of manufacturing a solid preparation comprising adding a methyl cellulose powder binder having an MeO content of 27.5–31.5 wt %, and whose 2 wt % aqueous solution has a viscosity of 2–12 cP at 20° C. to a powder of an active ingredient to form a mixed powder; forming a solid preparation of said mixed powder.

4. The method of claim 3, wherein said methyl cellulose is present in a blend ratio of 0.5–10 wt % of the solid preparation.

5. The solid preparation of claim 1, further comprising a lubricant.

6. The solid preparation of claim 2, further comprising a lubricant.

7. The method of claim 3, further comprising adding a lubricant to the mixed powder and forming a tablet.

8. The method of claim 4, further comprising adding a lubricant to the mixed powder and forming a tablet.

* * * * *